US009492208B1

(12) United States Patent
Arnold et al.

(10) Patent No.: US 9,492,208 B1
(45) Date of Patent: *Nov. 15, 2016

(54) SYSTEMS AND METHODS FOR HOLDING AND IMPLANTING BONE ANCHORS

(71) Applicant: NuVasive, Inc., San Diego, CA (US)

(72) Inventors: Benjamin Arnold, San Diego, CA (US); Eric Dasso, Carlsbad, CA (US); Justin Doose, San Diego, CA (US); Richard Mueller, Chapel Hill, NC (US); Robert German, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/947,461

(22) Filed: Nov. 20, 2015

Related U.S. Application Data

(63) Continuation of application No. 13/894,355, filed on May 14, 2013, now Pat. No. 9,192,415, which is a continuation of application No. 12/322,815, filed on Feb. 6, 2009, now Pat. No. 8,439,922.

(60) Provisional application No. 61/026,719, filed on Feb. 6, 2008.

(51) Int. Cl.
  *A61B 17/70* (2006.01)
  *A61B 17/90* (2006.01)

(52) U.S. Cl.
  CPC ....... *A61B 17/7082* (2013.01); *A61B 17/7083* (2013.01); *A61B 17/7086* (2013.01); *A61B 2017/90* (2013.01)

(58) Field of Classification Search
  CPC ........................... A61B 17/70; A61B 17/7082

USPC .............. 606/60, 86 A, 104, 105, 246–279, 606/300–331
See application file for complete search history.

(56) References Cited

U.S. PATENT DOCUMENTS

| 4,282,217 A | 8/1981 | Baglioni |
| 4,316,169 A | 2/1982 | Teranishi |
| 4,450,899 A | 5/1984 | Jakobsson |
| 4,655,216 A | 4/1987 | Tischer |
| 5,217,497 A | 6/1993 | Mehdian |
| 5,360,431 A | 11/1994 | Puno |
| 5,474,555 A | 12/1995 | Puno |
| 5,496,321 A | 3/1996 | Puno |
| 5,681,319 A | 10/1997 | Biedermann |
| 5,716,356 A | 2/1998 | Biedermann |

(Continued)

FOREIGN PATENT DOCUMENTS

| DE | 4238339 | 5/1994 |
| DE | 202012102895 U1 | 8/2012 |

(Continued)

*Primary Examiner* — Christopher Beccia
(74) *Attorney, Agent, or Firm* — Rory Schermerhorn

(57) ABSTRACT

Systems and methods for a guide assembly for introducing a bone anchor to an operative target site. The guide includes an outer sleeve and an inner sleeve. The outer sleeve has a distal anchor engaging end, a proximal end, and a central passage extending from the distal end to the proximal end. The inner sleeve may be situated in the central passage of the outer sleeve. The inner sleeve is movable being between a first position and a second position. The first position permits insertion of the bone anchor in the central passage. The second position releasably fixes the bone anchor to the guide assembly.

15 Claims, 11 Drawing Sheets

(56) References Cited

U.S. PATENT DOCUMENTS

| | | |
|---|---|---|
| 5,720,751 A | 2/1998 | Jackson |
| 5,910,141 A | 6/1999 | Morrison |
| 5,941,885 A | 8/1999 | Jackson |
| 6,059,786 A | 5/2000 | Jackson |
| 6,139,549 A | 10/2000 | Keller |
| 6,179,841 B1 | 1/2001 | Jackson |
| 6,183,472 B1 | 2/2001 | Lutz |
| 6,189,422 B1 | 2/2001 | Stihl |
| 6,224,598 B1 | 5/2001 | Jackson |
| 6,235,028 B1 | 5/2001 | Brumfield et al. |
| 6,251,112 B1 | 6/2001 | Jackson |
| 6,258,090 B1 | 7/2001 | Jackson |
| 6,299,616 B1 | 10/2001 | Beger |
| 6,379,356 B1 | 4/2002 | Jackson |
| 6,379,364 B1 | 4/2002 | Brace et al. |
| 6,440,132 B1 | 8/2002 | Jackson |
| 6,440,133 B1 | 8/2002 | Beale |
| 6,485,494 B1 | 11/2002 | Haider |
| 6,511,484 B2 | 1/2003 | Torode |
| 6,530,929 B1 | 3/2003 | Justis |
| 6,547,795 B2 | 4/2003 | Schneiderman |
| 6,554,834 B1 | 4/2003 | Crozet |
| 6,648,888 B1 | 11/2003 | Shluzas |
| 6,723,100 B2 | 4/2004 | Biedermann |
| 6,726,687 B2 | 4/2004 | Jackson |
| 6,743,231 B1 | 6/2004 | Gray |
| 6,884,244 B1 | 4/2005 | Jackson |
| 6,929,606 B2 | 8/2005 | Ritland |
| 6,951,538 B2 | 10/2005 | Ritland |
| 7,008,422 B2 | 3/2006 | Foley |
| 7,011,660 B2 | 3/2006 | Sherman |
| 7,073,415 B2 | 7/2006 | Casutt |
| 7,094,239 B1 | 8/2006 | Michelson |
| 7,160,300 B2 | 1/2007 | Jackson |
| 7,179,261 B2 | 2/2007 | Sicvol |
| 7,188,626 B2 | 3/2007 | Foley |
| 7,204,838 B2 | 4/2007 | Jackson |
| 7,250,052 B2 | 7/2007 | Landry |
| 7,278,995 B2 | 10/2007 | Nichols |
| D560,128 S | 1/2008 | Diederich |
| 7,470,279 B2 | 12/2008 | Jackson |
| 7,476,240 B2 | 1/2009 | Raymond |
| 7,481,813 B1 | 1/2009 | Purcell |
| 7,491,208 B2 | 2/2009 | Pond |
| 7,491,218 B2 | 2/2009 | Landry |
| 7,520,879 B2 | 4/2009 | Justis |
| 7,527,638 B2 | 5/2009 | Anderson |
| 7,563,264 B2 | 7/2009 | Landry |
| 7,574,318 B2 | 8/2009 | Hsieh |
| 7,588,575 B2 | 9/2009 | Colleran |
| 7,588,588 B2 | 9/2009 | Spitler |
| 7,608,081 B2 | 10/2009 | Abdelgany |
| 7,618,422 B2 | 11/2009 | Goodwin |
| 7,621,918 B2 | 11/2009 | Jackson |
| 7,648,521 B2 | 1/2010 | Hestad |
| 7,651,502 B2 | 1/2010 | Jackson |
| 7,678,139 B2 | 3/2010 | Garamszegi |
| 7,691,132 B2 | 4/2010 | Landry |
| 7,708,743 B2 | 5/2010 | Anderson |
| 7,708,763 B2 | 5/2010 | Selover |
| 7,717,944 B2 | 5/2010 | Foley |
| 7,744,629 B2 | 6/2010 | Hestad |
| 7,749,233 B2 | 7/2010 | Farr |
| 7,758,617 B2 | 7/2010 | Iott |
| 7,763,055 B2 | 7/2010 | Foley |
| 7,771,430 B2 | 8/2010 | Jones |
| 7,811,288 B2 | 10/2010 | Jones |
| 7,854,751 B2 | 12/2010 | Sicvol |
| 7,862,595 B2 | 1/2011 | Foley |
| 7,867,259 B2 | 1/2011 | Foley |
| 7,909,835 B2 | 3/2011 | Oribe |
| 7,914,558 B2 | 3/2011 | Landry |
| 7,918,857 B2 | 4/2011 | Dziedzic |
| 7,918,858 B2 | 4/2011 | Stad |
| 7,918,878 B2 | 4/2011 | Songer |
| 7,922,727 B2 | 4/2011 | Songer |
| 7,927,334 B2 | 4/2011 | Miller |
| 7,931,654 B2 | 4/2011 | Jones |
| 7,931,673 B2 | 4/2011 | Hestad |
| 7,947,045 B2 | 5/2011 | Hestad |
| 7,955,355 B2 | 6/2011 | Chin |
| 7,967,821 B2 | 6/2011 | Sicvol |
| 7,985,242 B2 | 7/2011 | Forton |
| 8,002,798 B2 | 8/2011 | Chin |
| 8,034,084 B2 | 10/2011 | Landry |
| 8,052,720 B2 | 11/2011 | Kuester |
| 8,062,340 B2 | 11/2011 | Berrevoets |
| 8,066,739 B2 | 11/2011 | Jackson |
| 8,075,592 B2 | 12/2011 | Landry |
| 8,100,915 B2 | 1/2012 | Jackson |
| 8,100,951 B2 | 1/2012 | Justis |
| 8,105,361 B2 | 1/2012 | Anderson |
| 8,137,355 B2 | 3/2012 | Hestad |
| 8,137,356 B2 | 3/2012 | Hestad |
| 8,137,387 B2 | 3/2012 | Garamszegi |
| 8,152,810 B2 | 4/2012 | Jackson |
| 8,162,948 B2 | 4/2012 | Jackson |
| 8,177,817 B2 | 5/2012 | Fallin |
| 8,192,439 B2 | 6/2012 | Songer |
| 8,192,440 B2 | 6/2012 | Jones |
| 8,231,635 B2 | 7/2012 | Sharifi-Mehr |
| 8,262,662 B2 | 9/2012 | Beardsley |
| 8,273,089 B2 | 9/2012 | Jackson |
| 8,277,491 B2 | 10/2012 | Selover |
| 8,292,892 B2 | 10/2012 | Jackson |
| 8,303,595 B2 | 11/2012 | Jones |
| 8,317,796 B2 | 11/2012 | Stihl |
| 8,361,124 B2 | 1/2013 | Sherman |
| 8,377,067 B2 | 2/2013 | Jackson |
| 8,439,922 B1 * | 5/2013 | Arnold ............... A61B 17/7086 606/104 |
| 8,460,300 B2 | 6/2013 | Hestad |
| 8,460,308 B2 | 6/2013 | Marino |
| 8,470,008 B2 | 6/2013 | Dickinson |
| 8,496,685 B2 | 7/2013 | Landry |
| 8,518,082 B2 | 8/2013 | Sicvol |
| 8,617,427 B2 | 12/2013 | Jiang |
| RE44,813 E | 3/2014 | Beale |
| 8,663,298 B2 | 3/2014 | Keyer |
| 8,679,128 B2 | 3/2014 | Seelig |
| 9,192,415 B1 * | 11/2015 | Arnold ............... A61B 17/7082 |
| 2001/0021853 A1 | 9/2001 | Heckele et al. |
| 2002/0072751 A1 | 6/2002 | Jackson |
| 2002/0133159 A1 | 9/2002 | Jackson |
| 2003/0199872 A1 | 10/2003 | Markworth |
| 2003/0208203 A1 | 11/2003 | Lim et al. |
| 2003/0225408 A1 | 12/2003 | Nichols |
| 2003/0236529 A1 | 12/2003 | Shluzas |
| 2004/0039383 A1 | 2/2004 | Jackson |
| 2004/0049196 A1 | 3/2004 | Jackson |
| 2004/0138662 A1 | 7/2004 | Landry et al. |
| 2004/0143265 A1 | 7/2004 | Landry et al. |
| 2004/0147937 A1 | 7/2004 | Dunbar, Jr. et al. |
| 2004/0158247 A1 | 8/2004 | Sitiso |
| 2004/0167523 A1 | 8/2004 | Jackson |
| 2004/0172022 A1 | 9/2004 | Landry et al. |
| 2004/0254576 A1 | 12/2004 | Dunbar |
| 2004/0267275 A1 | 12/2004 | Cournoyer |
| 2005/0021031 A1 | 1/2005 | Foley et al. |
| 2005/0065517 A1 | 3/2005 | Chin |
| 2005/0085813 A1 | 4/2005 | Spitler et al. |
| 2005/0131408 A1 | 6/2005 | Sicvol et al. |
| 2005/0131419 A1 | 6/2005 | McCord et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0154389 A1 | 7/2005 | Selover et al. |
| 2005/0176468 A1 | 8/2005 | Iacono et al. |
| 2005/0182410 A1 | 8/2005 | Jackson |
| 2005/0192570 A1 | 9/2005 | Jackson et al. |
| 2005/0192579 A1 | 9/2005 | Jackson |
| 2005/0192589 A1 | 9/2005 | Raymond et al. |
| 2005/0215999 A1 | 9/2005 | Birkmeyer et al. |
| 2005/0228380 A1 | 10/2005 | Moore et al. |

(56) References Cited

U.S. PATENT DOCUMENTS

| | | |
|---|---|---|
| 2005/0228400 A1 | 10/2005 | Chao et al. |
| 2005/0245928 A1 | 11/2005 | Colleran et al. |
| 2006/0003624 A1 | 1/2006 | Dow et al. |
| 2006/0036244 A1 | 2/2006 | Spitler et al. |
| 2006/0036254 A1 | 2/2006 | Lim |
| 2006/0036255 A1 | 2/2006 | Pond, Jr. et al. |
| 2006/0069391 A1 | 3/2006 | Jackson |
| 2006/0074418 A1 | 4/2006 | Jackson |
| 2006/0079894 A1 | 4/2006 | Colleran et al. |
| 2006/0079909 A1 | 4/2006 | Runco |
| 2006/0084993 A1 | 4/2006 | Landry et al. |
| 2006/0089651 A1 | 4/2006 | Trudeau et al. |
| 2006/0095035 A1 | 5/2006 | Jones et al. |
| 2006/0100622 A1 | 5/2006 | Jackson |
| 2006/0106380 A1 | 5/2006 | Colleran et al. |
| 2006/0106394 A1 | 5/2006 | Colleran et al. |
| 2006/0111712 A1 | 5/2006 | Jackson |
| 2006/0111713 A1 | 5/2006 | Jackson |
| 2006/0111715 A1 | 5/2006 | Jackson |
| 2006/0122597 A1 | 6/2006 | Jones et al. |
| 2006/0142761 A1 | 6/2006 | Landry et al. |
| 2006/0200132 A1 | 9/2006 | Chao et al. |
| 2006/0229614 A1 | 10/2006 | Foley |
| 2006/0247630 A1 | 11/2006 | Iott |
| 2006/0247658 A1 | 11/2006 | Pond, Jr. et al. |
| 2006/0264934 A1 | 11/2006 | Fallin |
| 2006/0276789 A1 | 12/2006 | Jackson |
| 2006/0281838 A1 | 12/2006 | Steinhausler et al. |
| 2006/0293684 A1 | 12/2006 | Shluzas |
| 2006/0293692 A1 | 12/2006 | Whipple |
| 2006/0293693 A1 | 12/2006 | Farr et al. |
| 2007/0043378 A1 | 2/2007 | Kumar |
| 2007/0049931 A1 | 3/2007 | Justis et al. |
| 2007/0065692 A1 | 3/2007 | Ryoo |
| 2007/0167949 A1 | 7/2007 | Altarac et al. |
| 2007/0167954 A1 | 7/2007 | Sicvol et al. |
| 2007/0213722 A1 | 9/2007 | Jones |
| 2007/0233155 A1 | 10/2007 | Lovell |
| 2007/0270811 A1 | 11/2007 | Dewey |
| 2007/0288002 A1 | 12/2007 | Carls et al. |
| 2007/0288007 A1 | 12/2007 | Burkus et al. |
| 2007/0299450 A1 | 12/2007 | Her et al. |
| 2008/0005787 A1 | 1/2008 | Aldred |
| 2008/0009864 A1 | 1/2008 | Forton |
| 2008/0015601 A1 | 1/2008 | Castro |
| 2008/0024937 A1 | 1/2008 | Gill et al. |
| 2008/0039844 A1 | 2/2008 | Jackson |
| 2008/0045957 A1 | 2/2008 | Wagner |
| 2008/0045970 A1 | 2/2008 | Saidha |
| 2008/0051787 A1 | 2/2008 | Remington et al. |
| 2008/0051794 A1 | 2/2008 | Dec |
| 2008/0073323 A1 | 3/2008 | Full et al. |
| 2008/0077135 A1 | 3/2008 | Stad et al. |
| 2008/0077138 A1 | 3/2008 | Cohen et al. |
| 2008/0086132 A1 | 4/2008 | Biedermann |
| 2008/0091213 A1 | 4/2008 | Jackson |
| 2008/0132904 A1 | 6/2008 | Usher et al. |
| 2008/0140132 A1 | 6/2008 | Perez-Cruet |
| 2008/0172062 A1 | 7/2008 | Donahue et al. |
| 2008/0234678 A1 | 9/2008 | Gutierrez |
| 2008/0243190 A1 | 10/2008 | Dziedzic |
| 2008/0275456 A1 | 11/2008 | Vonwiller et al. |
| 2008/0288005 A1 | 11/2008 | Jackson |
| 2008/0312703 A1 | 12/2008 | Hestad et al. |
| 2008/0319477 A1 | 12/2008 | Justis et al. |
| 2009/0030419 A1 | 1/2009 | Runco |
| 2009/0030420 A1 | 1/2009 | Runco |
| 2009/0048601 A1 | 2/2009 | Forton et al. |
| 2009/0082666 A1 | 3/2009 | Geist et al. |
| 2009/0099572 A1 | 4/2009 | Geist et al. |
| 2009/0105712 A1 | 4/2009 | Dauster |
| 2009/0131755 A1 | 5/2009 | White et al. |
| 2009/0143828 A1* | 6/2009 | Stad ............... A61B 17/7085 606/86 A |
| 2009/0149887 A1* | 6/2009 | Schlaepfer ......... A61B 17/7034 606/278 |
| 2009/0157125 A1 | 6/2009 | Hoffman |
| 2009/0171391 A1 | 7/2009 | Hutton et al. |
| 2009/0174467 A1 | 7/2009 | Kim |
| 2009/0216328 A1 | 8/2009 | Birkmeyer |
| 2009/0228053 A1 | 9/2009 | Kolb |
| 2009/0228054 A1 | 9/2009 | Hoffman |
| 2009/0228055 A1 | 9/2009 | Jackson |
| 2009/0240292 A1 | 9/2009 | Butler |
| 2009/0254125 A1 | 10/2009 | Predick |
| 2009/0306721 A1 | 12/2009 | Kirschman |
| 2010/0004696 A1 | 1/2010 | Jackson |
| 2010/0036434 A1 | 2/2010 | Ely |
| 2010/0057126 A1 | 3/2010 | Hestad |
| 2010/0063552 A1 | 3/2010 | Chin |
| 2010/0121385 A1 | 5/2010 | Blain |
| 2010/0160921 A1 | 6/2010 | Sun |
| 2010/0238572 A1 | 9/2010 | Tao |
| 2010/0292742 A1 | 11/2010 | Stad |
| 2010/0294595 A1 | 11/2010 | Osburn |
| 2011/0004222 A1 | 1/2011 | Biedermann |
| 2011/0034961 A1 | 2/2011 | Runco |
| 2011/0040328 A1 | 2/2011 | Miller |
| 2011/0040335 A1 | 2/2011 | Stihl |
| 2011/0077692 A1 | 3/2011 | Jackson |
| 2011/0106187 A1 | 5/2011 | Foley |
| 2011/0137358 A1 | 6/2011 | Manninen |
| 2011/0184469 A1 | 7/2011 | Ballard |
| 2011/0202137 A1 | 8/2011 | Keith |
| 2011/0218583 A1 | 9/2011 | Smith |
| 2011/0234466 A1 | 9/2011 | Yamada |
| 2011/0257692 A1 | 10/2011 | Sandstrom |
| 2011/0282402 A1 | 11/2011 | Chao |
| 2012/0078316 A1 | 3/2012 | Anderson |
| 2012/0100497 A1 | 4/2012 | Joo |
| 2012/0123431 A1 | 5/2012 | Robinson |
| 2012/0158070 A1 | 6/2012 | Jackson |
| 2012/0165876 A1 | 6/2012 | Nichols |
| 2012/0191144 A1 | 7/2012 | Peultier |
| 2012/0203288 A1 | 8/2012 | Lange |
| 2012/0271365 A1 | 10/2012 | Daubs |
| 2012/0277800 A1 | 11/2012 | Jackson |
| 2013/0035728 A1 | 2/2013 | Jackson |
| 2013/0035729 A1 | 2/2013 | Hammer |
| 2013/0072987 A1 | 3/2013 | Justis |
| 2013/0090697 A1 | 4/2013 | George |
| 2013/0110124 A1 | 5/2013 | Gleason |
| 2013/0184763 A1 | 7/2013 | McClintock |
| 2013/0296949 A1 | 11/2013 | Sicvol |
| 2013/0296950 A1 | 11/2013 | Landry |
| 2013/0304130 A1 | 11/2013 | Jackson |
| 2014/0031872 A1 | 1/2014 | Jackson |
| 2014/0031873 A1 | 1/2014 | Jackson |
| 2014/0039567 A1 | 2/2014 | Hoefer |
| 2014/0058465 A1 | 2/2014 | Nichols |
| 2014/0074106 A1 | 3/2014 | Shin |
| 2014/0100613 A1 | 4/2014 | Iott |
| 2014/0100617 A1 | 4/2014 | Sandstrom |
| 2014/0100618 A1 | 4/2014 | Kolb |
| 2014/0107708 A1 | 4/2014 | Biedermann |
| 2014/0163625 A1 | 6/2014 | Meyer |

FOREIGN PATENT DOCUMENTS

| | | |
|---|---|---|
| EP | 1470790 A1 | 10/2004 |
| EP | 1574175 A1 | 9/2005 |
| EP | 1767161 A1 | 3/2007 |
| EP | 1891904 A1 | 2/2008 |
| EP | 1929967 A1 | 6/2008 |
| EP | 1839606 A1 | 11/2008 |
| EP | 2324787 A1 | 5/2011 |
| EP | 2070485 A1 | 9/2011 |
| EP | 2462889 A1 | 6/2012 |
| EP | 2574297 A1 | 4/2013 |
| EP | 2719347 A1 | 4/2014 |
| FR | 2920663 A1 | 3/2009 |
| JP | 2003265492 A | 9/2003 |
| WO | WO-0128436 | 4/2001 |

(56) References Cited

FOREIGN PATENT DOCUMENTS

| WO | WO-02094114 | 11/2002 |
|----|-------------|---------|
| WO | WO-2004041100 | 5/2004 |
| WO | WO-2005058141 | 6/2005 |
| WO | WO-2006042188 | 4/2006 |
| WO | WO-2006057837 | 6/2006 |
| WO | WO-2006091863 | 8/2006 |
| WO | WO-2006127425 | 11/2006 |
| WO | WO-2007021588 | 2/2007 |
| WO | WO-2007038654 | 4/2007 |
| WO | WO-2007092056 | 8/2007 |
| WO | WO-2007092870 | 8/2007 |
| WO | WO-2007121271 | 10/2007 |
| WO | WO-2007149426 | 12/2007 |
| WO | WO-2008024937 | 2/2008 |
| WO | WO-2008039439 | 4/2008 |
| WO | WO-2008045719 | 4/2008 |
| WO | WO-2008051255 | 5/2008 |
| WO | WO-2008073323 | 6/2008 |
| WO | WO-2009012247 | 1/2009 |
| WO | WO-2012127267 | 9/2012 |
| WO | WO-2012127268 | 9/2012 |

* cited by examiner

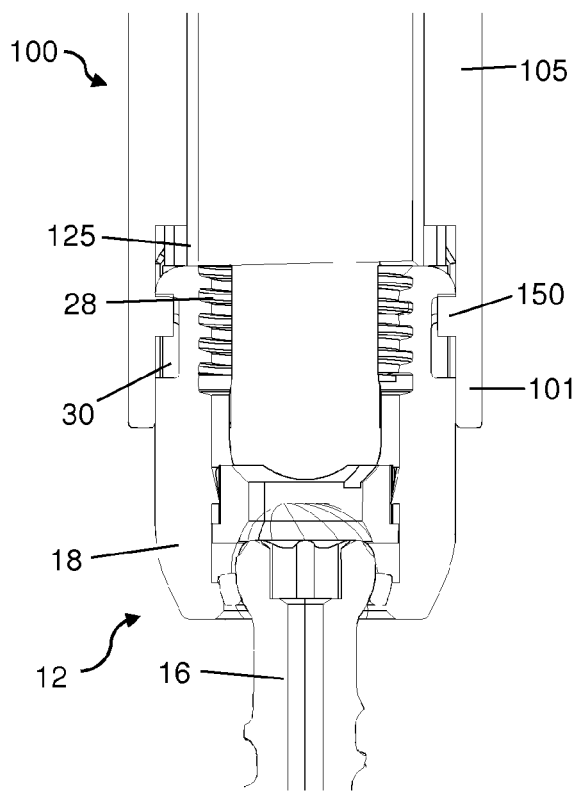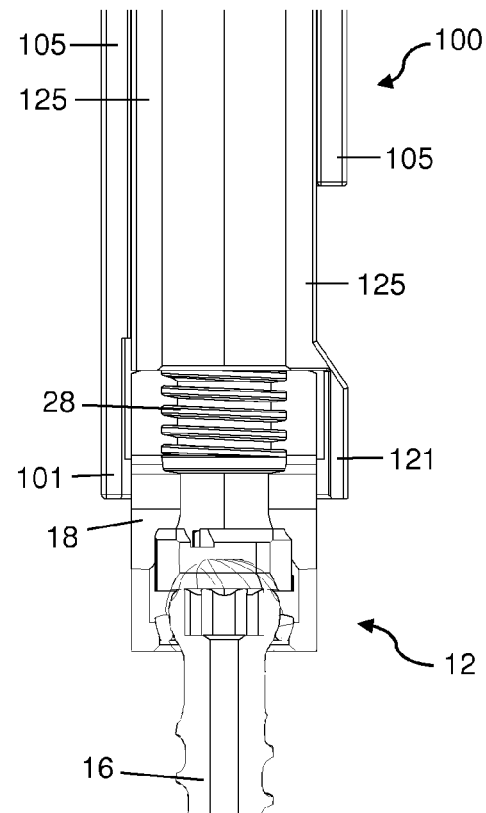
Fig. 6
Fig. 7

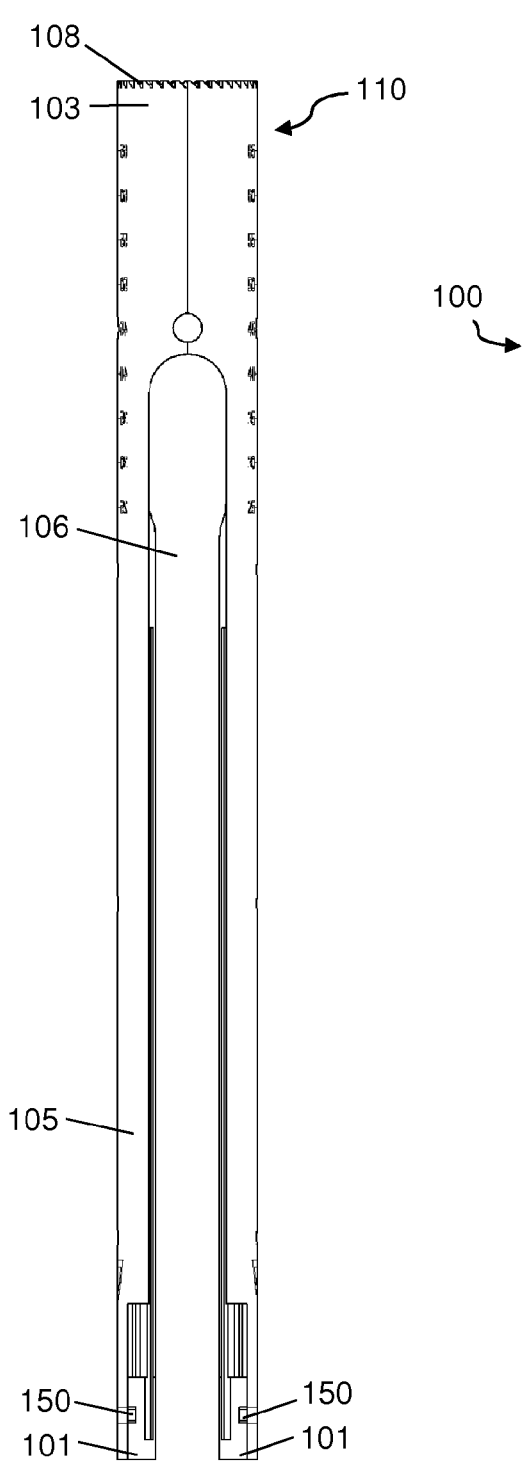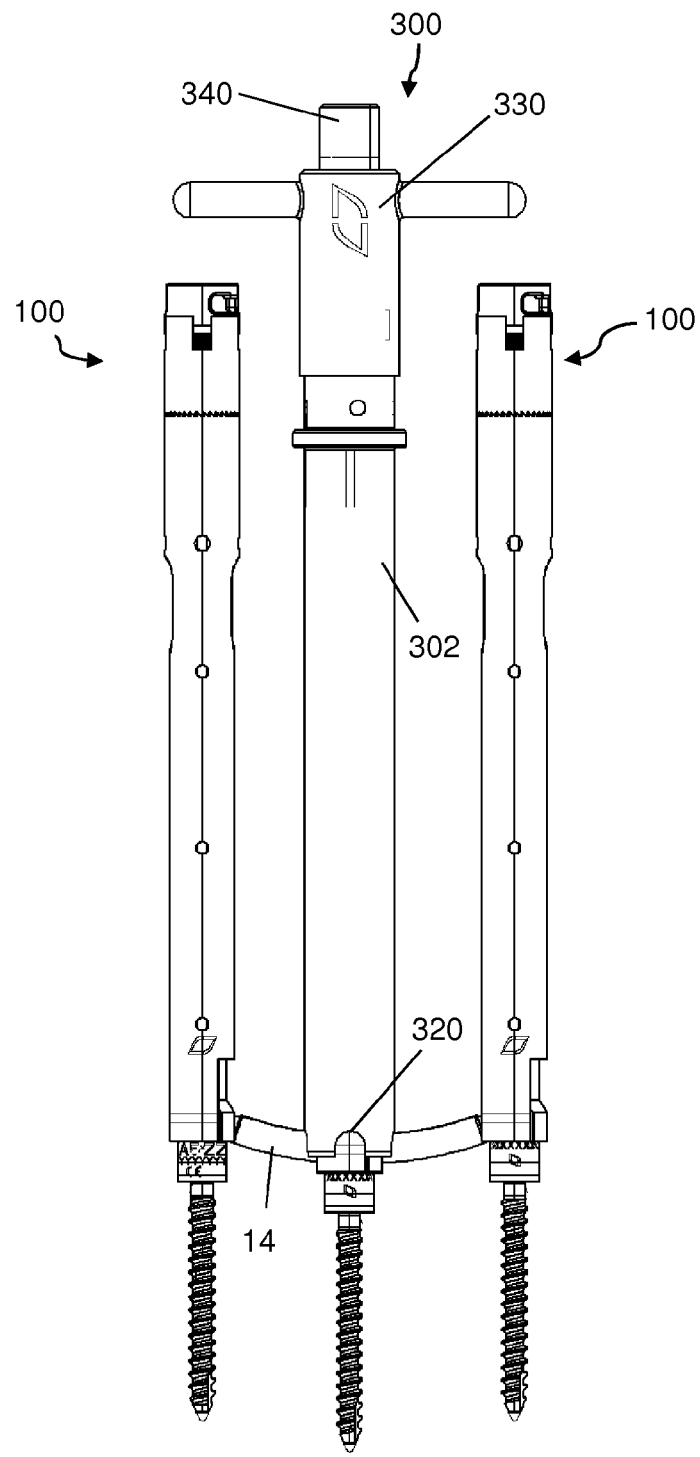
Fig. 15
Fig. 16

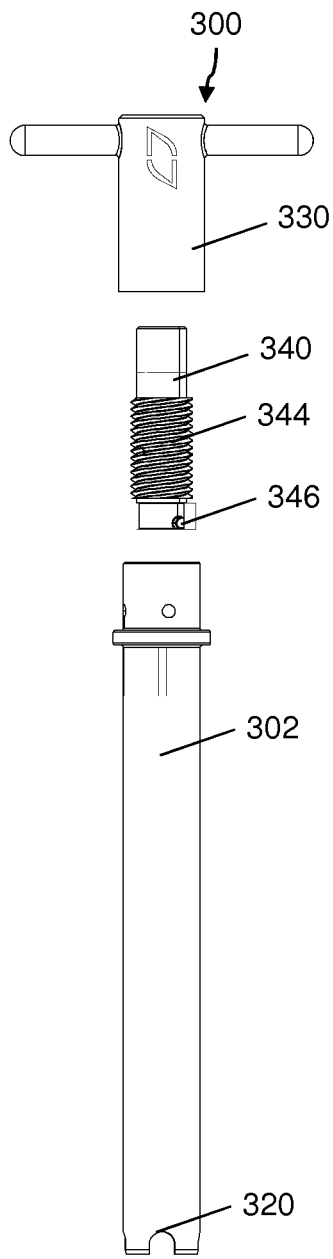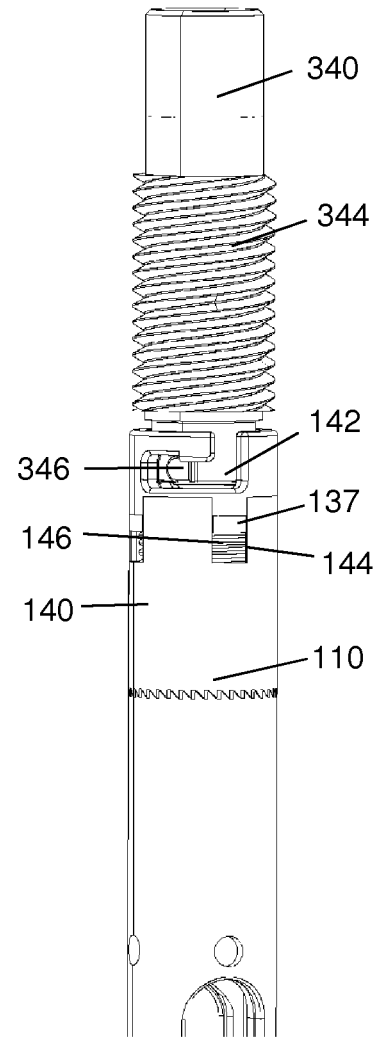
Fig. 17
Fig. 18

SYSTEMS AND METHODS FOR HOLDING AND IMPLANTING BONE ANCHORS

CROSS REFERENCE TO RELATED APPLICATIONS

This application is a continuation of U.S. patent application Ser. No. 13/894,355 filed May 14, 2013, pending, which is a continuation of U.S. patent application Ser. No. 12/322,815 filed Feb. 6, 2009, now U.S. Pat. No. 8,439,922, which claims the benefit of priority under 35 U.S.C. §119(e) from U.S. Provisional Patent Application No. 61/026,719 filed Feb. 6, 2008, the entire contents of which is hereby expressly incorporated by reference into this disclosure as if set forth fully herein.

BACKGROUND OF THE INVENTION

I. Field of the Invention

The present invention relates to medical devices and methods for deploying bone anchors to an implantation site.

II. Discussion of the Prior Art

Bone anchors are often surgically implanted into a patient as part of a spinal fixation or stabilization construct. Fixation systems are often to aid in the stabilization of a damaged spine or to aid in the correction of other spinal geometric deformities. Spinal fixation systems are often constructed as a framework stabilizing a particular section of the spine. Existing systems often use a combination of rods, plates, pedicle screws and bone hooks for fixing the framework to the affected vertebrae. The configuration required for each patient varies due to the patient's specific anatomical characteristics and ailments.

SUMMARY OF THE INVENTION

In one aspect of the invention, there is provided a guide assembly for introducing a bone anchor to an operative target site. The guide includes an outer sleeve and an inner sleeve. The outer sleeve has a distal anchor engaging end, a proximal end, and a central passage extending from the distal end to the proximal end. The inner sleeve may be situated in the central passage of the outer sleeve. The inner sleeve is movable being between a first position and a second position. The first position permits insertion of the bone anchor in the central passage. The second position releasably fixes the bone anchor to the guide assembly.

According to another aspect of the invention, there is provided a guide assembly for introducing a bone anchor to an operative target site. The bone anchor includes a housing having a pair of opposed arms. There is an outer sleeve and an inner sleeve. The outer sleeve has a distal end, a proximal end, and a central passage extending from the distal end to the proximal end. The distal end of the outer sleeve includes first and second lateral projections dimensioned to engage first and second recesses formed in the housing. The distal end also includes first and second longitudinal ridges dimensioned to be received within first and second longitudinal grooves formed in the housing. The inner sleeve has a distal end and a proximal end. The inner sleeve may be situated in the central passage and moveable along a longitudinal axis between an open position and a closed position. The closed position temporarily fixes the housing to the guide assembly. The inner sleeve further includes third and fourth longitudinal ridges that are received within third and forth longitudinal grooves in the housing when the inner tube is in a closed position. In some implementations the guide assembly may include a locking element.

BRIEF DESCRIPTION OF THE DRAWINGS

The invention will be more fully understood from the following detailed descriptions taken in conjunction with the accompanying drawings, in which:

FIG. 6 is a cross section view of the proximal end of the guide assembly of FIG. 2;

FIG. 7 is a cross section rotated 90 degrees for view of the proximal end of the guide assembly of FIG. 6;

FIG. 15 is a side view of an alternate guide assembly, according to another embodiment of the present invention; and FIGS. 16-18 illustrate the insertion and locking of the pedicle screw assembly into the distal portion of the guide assembly.

DESCRIPTION OF THE PREFERRED EMBODIMENT

Illustrative embodiments of the invention are described below for the purposes of understanding the principles of the invention. No limitation of the scope of the invention is therefore intended. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system disclosed herein boasts a variety of inventive features and components that warrant patent protection, both individually and in combination.

Figure 1:
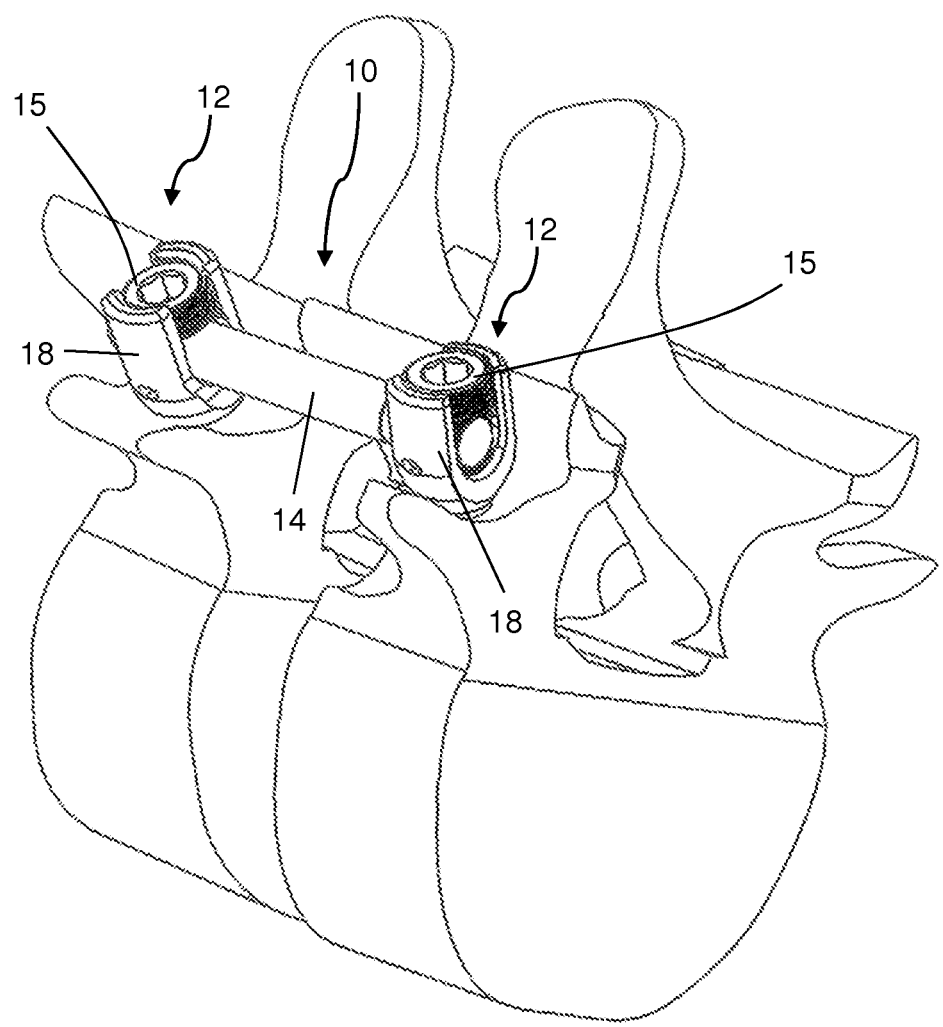
FIG. 1 is a perspective view of a spinal fixation construct including a pair of bone anchors, fasteners and, including (by way of example only) first and second pedicle screws and a connecting element.

With reference to FIG. 1, a pair of bone anchors 12 are shown as they might be utilized to form a spinal fixation construct 10 (including the pair of anchors, a rigid connecting element 14 linking the bone anchors, and a pair of fasteners 15 for securing the connecting element 14 to the bone anchors 12) for preventing movement between a pair of adjacent vertebra. The bone anchors 12 include an anchor element 16 configured for purchase within the bone, for example, a screw, at the implantation site and a housing 18 for coupling the bone anchor to the connecting element 14. The housing 18 may be fixed to the anchor element 16 or the housing 18 may be coupled to the anchor element 16 such that the housing may move in one or more planes relative to the anchor element 16. The housings 18 include two arms separated by a pair of slots which collectively form a generally "U-shaped" structure defining or containing an area dimensioned to receive the connecting element 14 and thereafter the locking screw 15 (e.g. a threaded lock screw). In some implementations the connecting element 14 may be flexible to provide support and stabilize the adjacent vertebrae without limiting all motion therebetween. Also, more than two bone anchors 12 may be used to link three or more vertebra together (e.g. multi-level). The bone anchors 12 may be positioned on both sides of the spine forming a bi-lateral construct. The bone anchors 12 may also be anchored in implantation sites other than the pedicles show, for example only, the bone anchors 12 could be implanted in the anterolateral aspect of the vertebral body.

Figure 2:
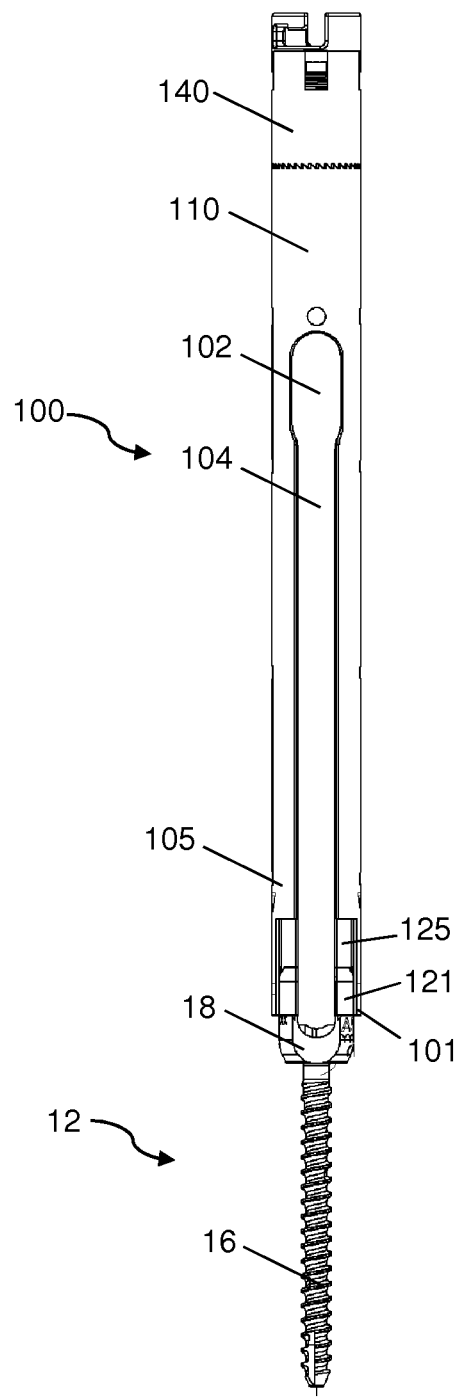
FIG. 2 is front view of a guide assembly of couple to a bone anchor according to one embodiment of the present invention.

Turning to FIG. 2, there is illustrated an example embodiment of a guide assembly 100 operable to temporarily engage and hold a bone anchor 12 and aid in the implantation of the bone anchor at a desired implantation site. The guide assembly 100 securely grasps the housing 18 of the bone anchor 12. The length of the guide assembly is generally provided such that at least a portion of the assembly will extend beyond a skin incision when an attached bone anchor 12 is fully implanted in the target site. Thus a surgeon may manipulate the guide assembly 100 from a position outside the operative corridor to advance and position the bone anchor in the desired location. An instrument (not shown) may be advanced through the guide assembly 100 to engage the anchor portion 16 and drive the anchor portion in to the target bone. Slots 104 may be provided in the guide assembly 10 to further help guide a connecting element into to the bone anchor housing 18.

Figure 3:
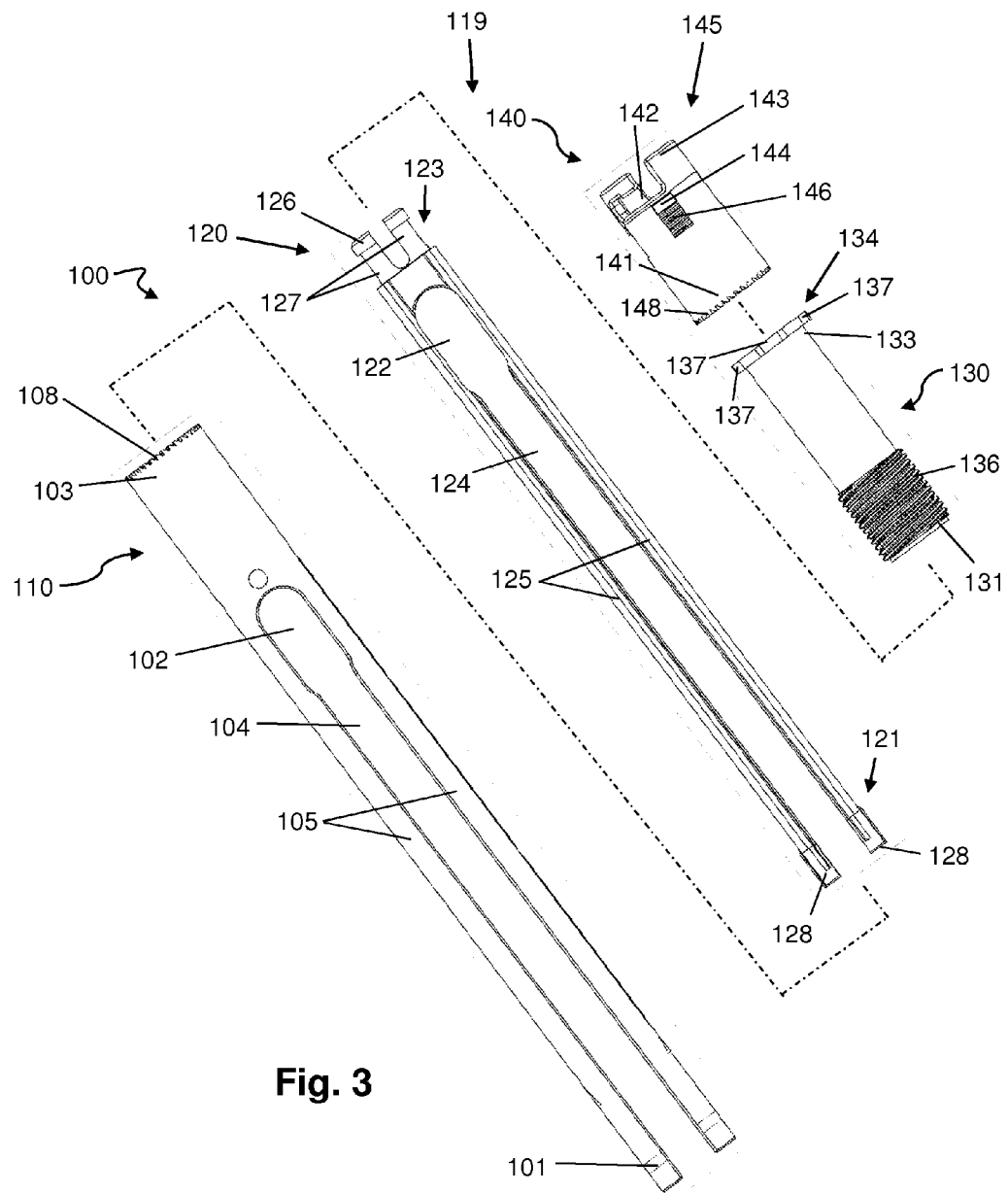
FIG. 3 is an exploded view the guide assembly of FIG. 2.
Figure 4:
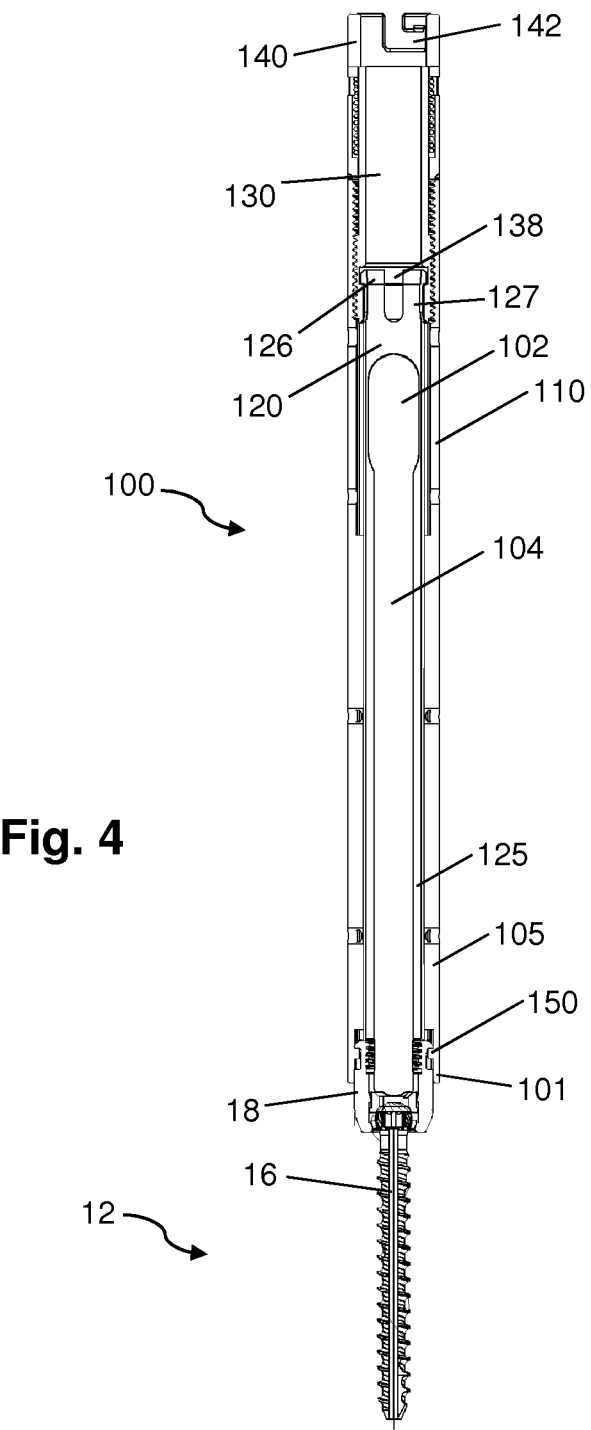
FIG. 4 is a cross section view of the guide assembly of FIG. 2.
Figure 5:
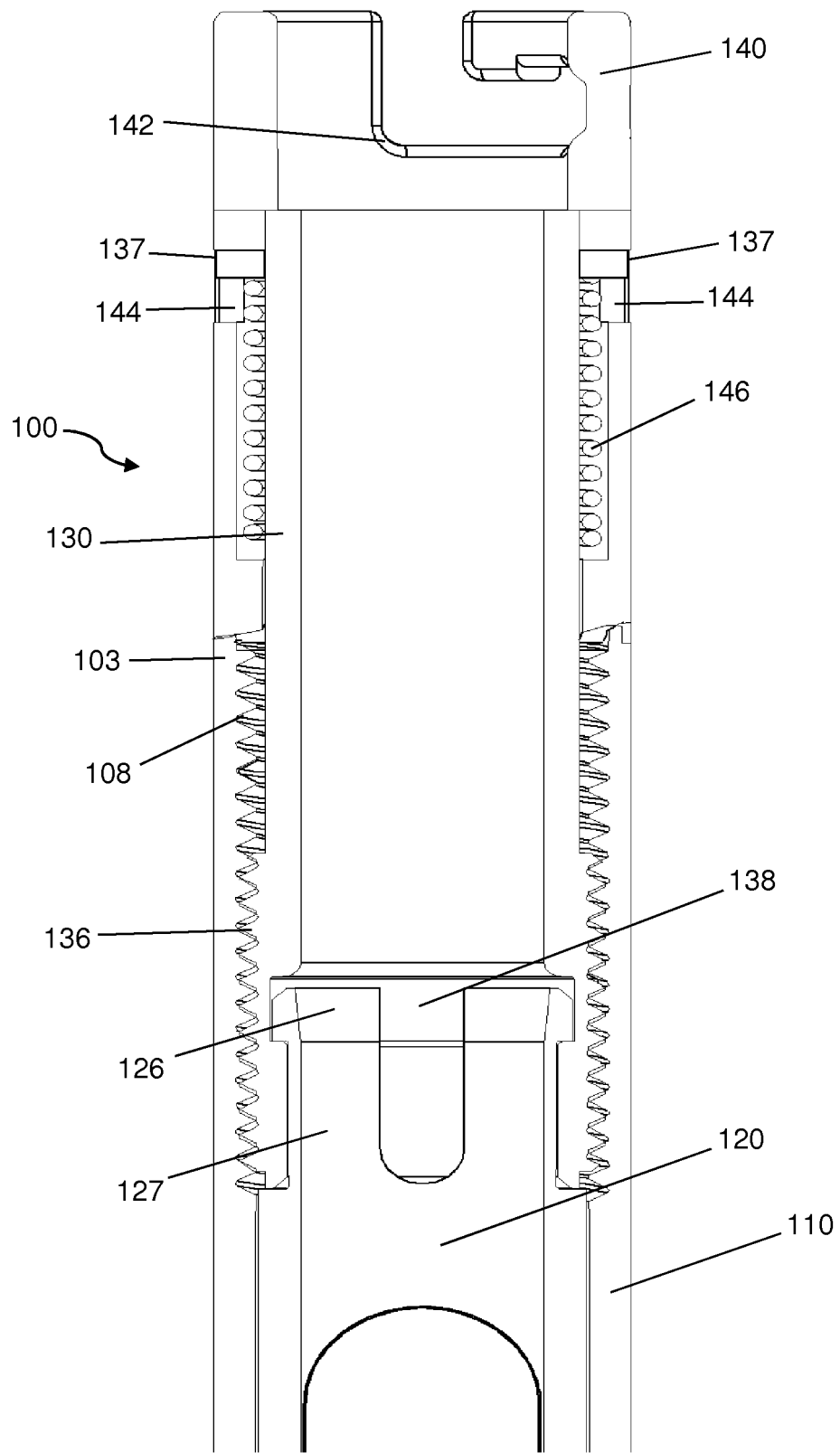
FIG. 5 is a cross section view of the a proximal portion of the guide assembly of FIG. 2.
Figures 8, 9:
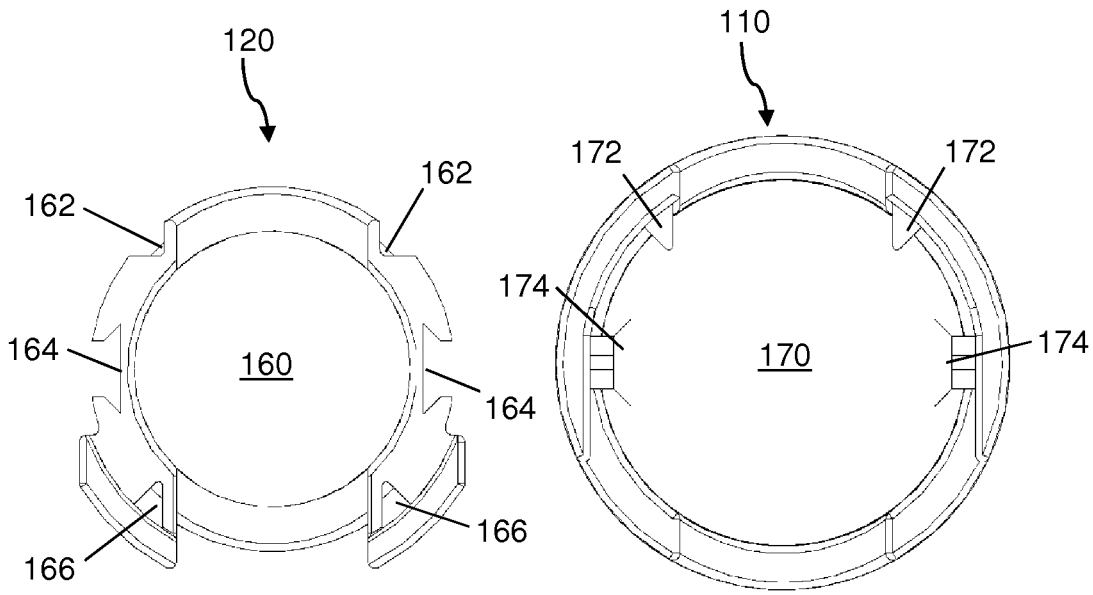
FIG. 8 is an end view of the inner guide member of FIG. 2.
FIG. 9 is a longitudinal view of the outer guide member of FIG. 2.

As shown in FIG. 3-5, the guide assembly 100 includes an outer sleeve 110 and an inner sleeve 120. The outer sleeve 110 may be generally cylindrical in shape and have a length extending from a distal end 101 configured to engage bone anchors to a proximal end 103. The length is dimensioned such that the proximal end 103 will extend beyond the skin entry site when the distal end 101 is positioned adjacent an implantation target site. A central passageway 170 (as shown in FIG. 9) extends through the outer sleeve from the distal end 101 to the proximal end 103. The outer sleeve 110 may further include a pair of opposed slots 104 opening at the distal end 101 and extending longitudinally along the outer sleeve to a position short of the proximal end. Preferably, slots 104 have a length great enough such that the proximal end of the slot remains outside the patient entry site when the distal end 101 of the outer sleeve 110 is adjacent the implantation site. Keyholes 102 having a width greater than the width of the slots 104 may be provided, connecting to the slots 104 at the proximal ends of slots 104. The keyholes 102 allow a connecting element 14 having one or more enlarged ends, as in FIG. 1, to be advanced into the slots 104. Together, the central passageway 170, open distal end 101, and opposed slots 104 generally divide the outer sleeve 110 into two halves or arms 105.

The inner sleeve 119 includes a main sleeve 120, a sleeve extension 130, and a cap 140. In general, the inner sleeve 119 has a generally cylindrical shape extending from a distal end 121 to a proximal end 145 and an interior passageway 160 (FIG. 12) extending between the distal end 121 and the proximal end 145. The length of inner sleeve 119 is preferably such that when the distal end 121 is positioned adjacent an implantation target site, the proximal end 145 extends beyond the proximal end 103 of the outer sleeve. The inner sleeve 119 is situated in the outer sleeve 110 and configured to translate longitudinally along a longitudinal axis relative to the outer sleeve in order to engage a portion of the bone anchor housing 18 and temporarily fix the bone anchor to the guide assembly.

The main sleeve 120 is situated within the central passageway 170 of the outer sleeve. The inner sleeve 120 may further include a pair of opposed slots 124 alignable with the slots 104 of the outer sleeve. The slots 104 open at the distal end 121 and extend longitudinally along the outer sleeve to a position short of the proximal end 123 of the main sleeve. Preferably, slots 124 have a length that is the same or similar to the slots 104 in outer sleeve 110. Keyholes 122 having a width greater than the width of the slots 124 may be provided, connecting to the slots 124 at the proximal ends of slots 124. Slots 104 of the outer sleeve 110 and slots 124 of the main sleeve 120 may have widths of approximately the same dimension selected such that a connecting element 14 may pass along the slots. Together, the interior passageway 160, open distal end 121, and opposed slots 124 generally divide the main sleeve 120 into two halves or arms 125.

The sleeve extension 130 is configured to join with the main sleeve 120 and may have a generally cylindrical shape. The sleeve extension 130 has a distal end 131 and a proximal end 133. The sleeve extension 130 has an interior lumen that extends from the distal end 131 to the proximal end 133 and forms part of interior passageway 160. Sleeve extension 130 and main sleeve 120 are joined such that they are longitudinally fixed relative to each other but can rotate freely about a longitudinal axis relative to each other. To accomplish this, two or more tabs 127 are situated at the proximal end 123 of the main sleeve and include radial ridges 126. A complementary radial groove 138 is provided in an inner wall of the sleeve extension 130 and receives the radial ridges thus preventing the longitudinal motion the main sleeve 120 and sleeve extension 130. Sleeve extension 130 is also fashioned with threaded region 136 dimensioned to engage threads 108 situated along a portion of the inner wall of outer sleeve 110 (best viewed in FIG. 9). At the proximal end 133 of the sleeve extension 130 a series of tabs 137 protrude laterally from a ring 134 for coupling the cap 140 via a series of corresponding apertures 144 in the cap.

The cap 140 is situated on the proximal end of the sleeve extension 130 and provides a grip for rotating the sleeve extension 130 in order to advance the threaded region 136 along the outer sleeve threads 108, thereby longitudinally adjusting the position of the inner sleeve 119 relative to the outer sleeve 110. The cap 140 has at least two slots 142 opening at the proximal end 143 for coupling a reduction extension, described below.

According to one example, the cap 140 may form part of a locking mechanism that prevents the guide assembly 100 from disengaging from the bone screw housing 18 until a user disengages the locking mechanism. The locking mechanism may comprise a series of teeth 148 situated about the distal end 143 of the cap 140 and a complementary series of teeth 108 situated about the proximal end 103 of the outer sleeve 110. According to one example the teeth 108 generally include a perpendicular face and a sloped face. Likewise, the teeth 148 also each include a perpendicular face and a sloped face. The teeth 108 and 148 are further arranged so that when the cap 140 is rotated, for example, in a clockwise direction to translate the inner sleeve 119 toward the distal end 101 (to affix the bone anchor housing 18) the sloped faces of teeth 108 and 148 engage, allowing the teeth to slide past each other. When the cap 140 is rotated in the opposite direction to translate the inner sleeve 119 toward the proximal end 103 (to detach the bone anchor housing 18) the perpendicular faces of teeth 108 and 148 will engage, preventing further rotation in that direction. To disengage the locking mechanism, the cap 140 is simply pulled in a direction away from the outer sleeve. To make the cap 140 longitudinally movable relative to the sleeve extension 130, the apertures 144 are provided with a height greater than the height of the tabs 137. Additionally, the cap 140 may be biased towards the most distal position such that the locking mechanism automatically engages as the inner sleeve 119 is translated through the outer sleeve 110 toward the distal end. This may be accomplished, for example, by positioning a spring 146 between cap 140 and the sleeve extension 130.

Figure 10:
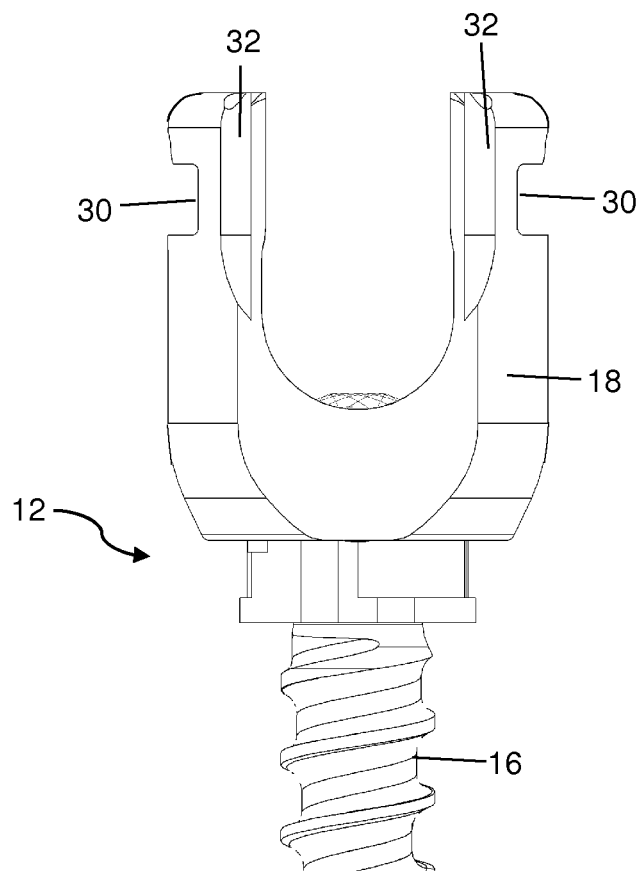
FIG. 10 is a side view of the bone anchor housing; according to one embodiment of the present invention.
Figure 11:
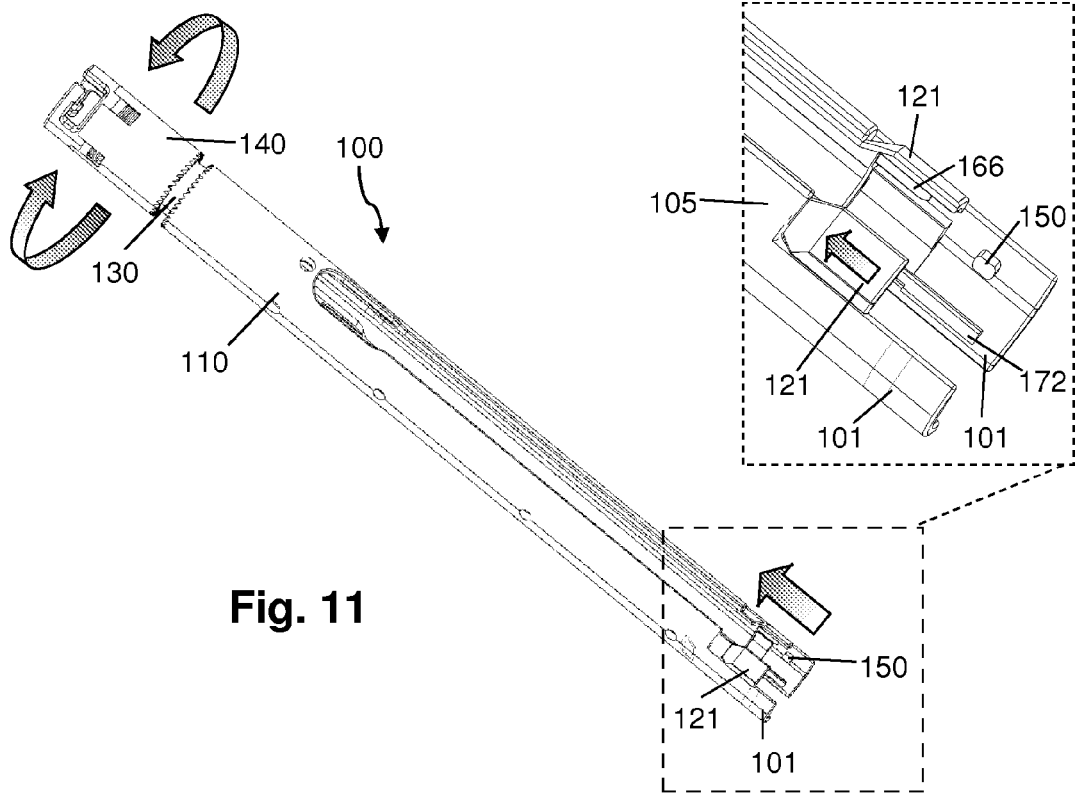
FIGS. 11-14 illustrate the insertion and locking of the bone anchor into the guide assembly of FIG. 2, according to one embodiment of the present invention.
Figure 12:
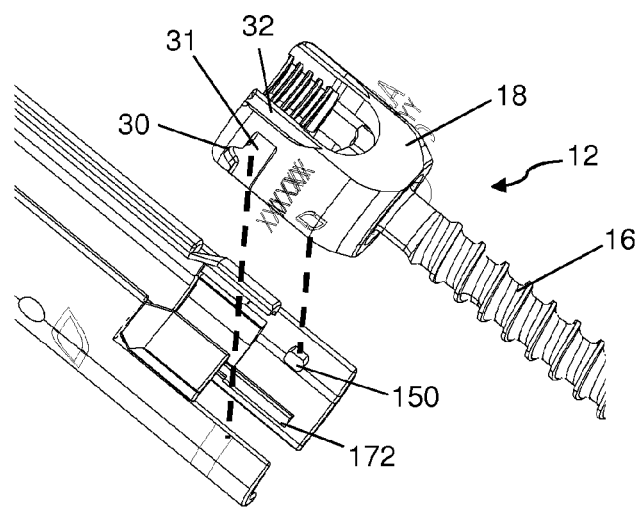
Figure 13:
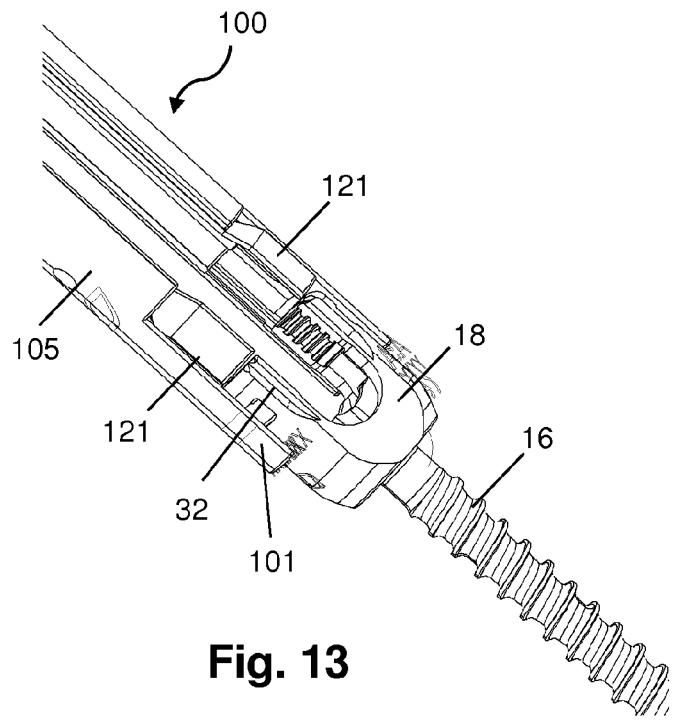

With reference to FIGS. 6-14, the guide assembly 100 securely engages the bone anchor 12 at the distal end. The central passageway 170 of the outer sleeve is dimensioned to receive the housing 18 at the distal end 103. A cutout region, best viewed in FIG. 12, provides an access path for side loading the housing 18 into the central passage way 170. Once the housing is loaded, the inner sleeve 120 is advanced distally toward the housing, by rotating the inner sleeve clockwise (by way of example). When the inner sleeve moves towards the distal end, distal extensions 128 block the cutout region such that the housing 18 cannot be removed.

Each arm 105 of outer sleeve 110 includes a lateral projection tab 150 near the distal end 101 of the outer sleeve 110. The tabs 150 are dimensioned to engage a recess 30 found on the outer wall of the screw housing 18 as shown in FIG. 6. Slots 31 situated below and in communication with the recess 30 allow the housing to be side loaded onto the tabs 150.

With reference to FIGS. 8 and 9, within the interior passageway 160, longitudinal ridges 166 are situated on the distal extensions 128. Each protrusion 166 is dimensioned to fit in a longitudinal groove 32 in the housing 18. In addition, two grooves 162, located on the outer portion of the inner sleeve 120 and opposite of the longitudinal ridges 166, are dimensioned to receive longitudinal ridges 172 of the outer sleeve 110. A channel 164 is also provided in the outer wall of the inner sleeve 120. Grooves 162 and channels 164 extend from the distal end 121 to a position near the proximal end 123 of the main sleeve 120.

Within the central passageway 170 of outer sleeve 110, a longitudinal ridge 172 is situated on each arm 105 of the outer sleeve 110. Similarly, a tab 174 is also situated on each arm 105. Each protrusion 172 and tab 174 extend from the distal end 101 to a position near the proximal end 103 of the outer sleeve 120.

The tabs 174 are dimensioned to engage the channels 164 of the inner sleeve 120, such that the tabs 174 will slide within the channels 164. As illustrated in FIGS. 8-9, and by example only, the tabs 174 and channels 164 have a dovetail configuration. The protrusions 172 are dimensioned to slide within the grooves 162 of the inner sleeve 120. The interaction between the tabs 174 and the channels 164 and between the protrusions 172 and the grooves 162, the main sleeve 120 may translate longitudinally within the outer sleeve 110 while rotation of the main sleeve 120 is prevented.

Turning to FIG. 10, each arm of the bone anchor housing 18 has two longitudinal grooves 32, one on each end of the arm. One groove 32 of each arm receives the longitudinal ridge 166 of the inner sleeve 120 and the other longitudinal groove 32 engages the protrusion 172 of the outer sleeve. In addition, each arm of the housing 18 has a recess 30 dimensioned to engage the tab 150 of the outer sleeve 110. As seen in FIG. 16, each recess 30 communicates with a rectangular slot 31. The slot 31, allows the tab 150 to slide horizontally along the arm so the tab 150 engage the recess 30. Thus, when the bone anchor housing 18 is loaded in the guide assembly 100 and the inner sleeve 119 is moved into closed position, the housing 18 and guide assembly 100 are positively engaged in six locations providing a secure attachment.

FIGS. 11-14 illustrate the process of attaching the guide assembly 100 to the screw assembly 12. First (if the guide assembly is in a "closed" position), as illustrated in FIG. 11, the user pulls the cap to disengage the teeth 108 and 148. The user may then rotate the cap 140 counterclockwise (by way of example). Turning the cap 140 rotates the sleeve extension 130 whereby the threaded region 136 travels proximally along the threads 108 of the outer sleeve 110, translating the inner sleeve 119 proximally relative to the outer sleeve 110. This results in the distal end of the guide assembly 100 moving to an "open" position Next, as shown in FIG. 12, bone anchor housing 18 is positioned in the guide assembly 100. The housing 18 is loaded into the central passageway 170 through the cutout region and the recesses 30 are engaged with the lateral projection tabs 150 two grooves 32 of the housing 18 will each receive a longitudinal ridge therein. At this stage the housing 18 is loosely held by the outer sleeve 110 only.

As shown in FIG. 18 to fully secure the bone anchor 12 in the guide assembly, the user will rotate the cap 140 clockwise. This causes the inner sleeve 120 to translate distally relative outer sleeve 110. As the inner sleeve 120 travels distally, the longitudinal ridges 166 on distal extension 128 of the inner sleeve will each engage the remaining grooves 32 of the housing 18. As the inner sleeve 119 approaches the closed or locked position locking mechanism will automatically engage as the teeth 108 and 148 meet. Once the bone anchor 12 is secured, the guide assembly may be advanced through an incision in the patient and to the implantation target site.

FIGS. 16-18 illustrate a reduction assembly 300 that may be utilized with the guide assembly 100. The reduction assembly 300 is configured to apply force to draw the housing 18 and a connecting element 14 deployed via the guide assembly 100 together prior to introducing a fastener 15. FIG. 16 depicts the reduction assembly 300 in position over a center guide assembly for deploying a multi-level construct. FIG. 17 illustrates an exploded view of the reduction assembly 300. The reduction assembly consists of a reduction sleeve 302, a reducer extension 340, and a reduction handle 330. The reduction sleeve 302 has a generally cylindrical shape with an inner lumen (not shown) dimensioned to slide over the guide assembly 100. At the distal end, openings 320 at opposite ends of the reduction sleeve 302 are dimensioned to engage the connective element 14.

With reference to FIG. 18, the tabs 346 of the reducer extension 340 engage the slots 142 of the cap 140. When the cap is "locked", meaning the teeth 148 have engaged the teeth 108 of the outer sleeve 110, a user will insert the tabs 346 into the openings of the angled slots 142. The user will then rotate the reducer extension 340 clockwise 90 degrees until the tabs 346 are locked within the angled slots 142. The threads 344 of the reducer extension 340 engage the threads, not shown, of the reduction handle 330. The reduction handle 330 is a generally cylindrical in shape with a grip and an inner lumen that contains threads. The distal end of the inner lumen is also dimensioned to receive the proximal end of the reduction sleeve 330.

While the housing is still fixed in the guide assembly 100 and after the anchors have all been implanted in the target bone the user attaches the reducer extension 340 to the cap 140. Then the user slides the reduction sleeve 302 over the guide assembly, aligning the openings 320 to engage the connecting element 14. Finally the user slides the reduction handle 330 over the reducer extension and rotates the handle clockwise to engage the threads 344 and the threads within the reduction handle 330. The reduction handle 330 engages the proximal end of the reduction sleeve 302 and as the reduction handle 330 is rotated clockwise a force is applied on the reduction sleeve 302 drawing the housing 18 and connecting element 14 together.

Figure 14:
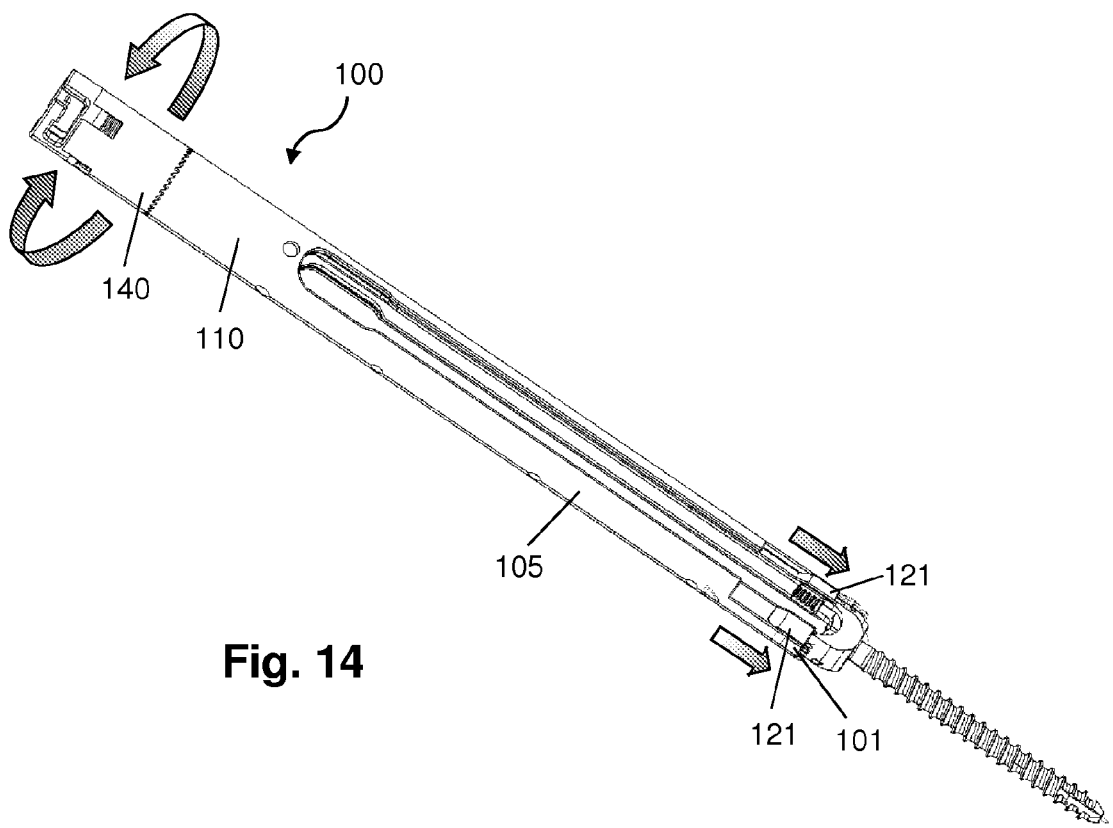

While the invention is susceptible to various modifications and alternative forms, specific embodiments thereof have been shown by way of example in the drawings and are herein described in detail. By way of example, an alternative guide assembly having opposing slots of different widths and/or without keyholes (as shown in FIG. 14) may be utilized to accommodate enlarged ends on some connecting elements. In addition, it is within the scope of the invention to introduce various types of bone anchors, including but not limited to a pedicle or hook anchor. The description herein of specific embodiments is not intended to limit the invention to the particular forms disclosed, but on the contrary, the invention is to cover all modifications, equivalents, and alternatives falling within the spirit and scope of the invention.

What is claimed is:

1. A guide assembly for introducing a bone anchor to an operative target site, the bone anchor including a housing having a pair of opposed arms defined by first and second opposed slots formed in the housing, comprising:

an outer sleeve having a distal end, a proximal end, a central passage extending from the distal end to the proximal end, the outer sleeve being divided into a first outer arm and a second outer arm, the first outer arm and second outer arm being separated by a third slot open at the distal end and a fourth slot opposite the third slot and open at the distal end, wherein the first outer arm includes a first projection at the distal end extending into the central passage and the second outer arm includes a second projection at the distal end extending into the central passage, the first and second projections configured to engage first and second recesses formed in the housing arms, a first inner arm slidably coupled to the first outer arm such that the first inner arm translates longitudinally relative to the first outer arm, and a second inner arm slidably coupled to the second outer arm such that the second inner arm translates longitudinally relative to the second outer arm, the first inner arm and second inner arm being separated by a fifth slot and a sixth slot, the fifth slot being aligned with the third slot of the outer sleeve and the sixth slot being aligned with the fourth slot of the outer sleeve, the third and fifth slot together being aligned with the first slot of the housing and the fourth and sixth slot together being aligned with the second slot of the housing when the first and second projections are engaged in the first and second recesses of the housing, the first inner arm and second inner arm moveable between an open position and a closed position for temporarily fixing the housing to the guide assembly, the first inner arm having a first distal extension with a first longitudinally extending engagement feature configured to slideably engage a complementary first longitudinally extending engagement feature on the housing when the first inner arm moves from the open position, the second inner arm having a second distal extension with a second longitudinally extending engagement feature configured to slideably engage a complementary second longitudinally extending engagement feature on the housing when the second inner arm moves from the open position, a proximal body threadedly engaged with internal threading of the outer sleeve and rotatable to translate the first inner arm and second inner arm between the open and closed positions.

2. The guide assembly of claim 1, wherein the distal end of the outer sleeve includes a cutout between the first outer arm and second outer arm, the first distal extension and second distal extension being situated within the cutout region.

3. The guide assembly of claim 2, wherein the cutout region is dimensioned to pass the bone anchor housing such that said housing is permitted to be introduced into the central passageway from the side when the first inner arm and second inner arm are in the open position.

4. The guide assembly of claim 1, further comprising a locking mechanism to prevent the proximal body from rotating to move the first inner arm and second inner arm from the closed position until the locking mechanism is disengaged.

5. The guide assembly of claim 4, wherein the locking mechanism automatically engages when the first inner arm and second inner arm move into the closed position.

6. The guide assembly of claim 5, wherein the locking mechanism includes a cap coupled to the proximal body.

7. The guide assembly of claim 6, wherein the proximal end of the outer sleeve comprises a set of proximal facing teeth and a distal end of the cap includes a complementary set of distal facing teeth.

8. The guide assembly of claim 7, wherein the proximal facing teeth and distal facing teeth each include a perpendicular face and a sloped face such that the sloped faces slide past each other when the cap is rotated in one direction and the perpendicular faces engage each other when the cap is rotated in the opposite direction.

9. The guide assembly of claim 8, wherein the cap is spring biased distally.

10. The guide assembly of claim 9, wherein the cap includes at least two apertures that receive corresponding tabs extending from the proximal body to couple the cap to the proximal body.

11. The guide assembly of claim 1, wherein an inner surface of the proximal body includes a circumferential groove that receives ridges associated with the first and second inner arms to longitudinally fix the first and second inner arms to the proximal body.

12. The guide assembly of claim 1, wherein the first inner arm includes a longitudinal channel that receives a longitudinal projection on an inner surface of the first outer arm and the second inner arm includes a longitudinal channel that receives a longitudinal projection on an inner surface of the second outer arm.

13. The guide assembly of claim 12, wherein the longitudinal channels and longitudinal projections have a dovetail configuration.

14. The guide assembly of claim 1, wherein the distal end of the outer sleeve includes third and fourth longitudinally extending engagement features configured to slideably engage complementary third and fourth longitudinally extending engagement features on the housing.

15. The guide assembly of claim 1, further comprising:
a reduction sleeve having a distal end, a proximal end, and a lumen dimensioned to slidably receive the outer sleeve therein;
a reduction extension releasably attachable to a proximal end of the guide assembly and comprising a thread formed about an outer surface of the reduction extension; and
a handle comprising a lumen with an internal thread complementary to the thread formed on the reduction extension such that rotation of the handle causes the handle to move along the longitudinal axis, wherein the handle contacts the proximal end of the reduction sleeve and advancing the handle along the reduction extension towards the bone anchor causes the reduction sleeve to advance along the outer sleeve toward the bone anchor such that an elongate element in contact with the distal end of the reduction sleeve may be persuaded towards the bone anchor housing.

* * * * *